US008986371B2

(12) United States Patent
Quill et al.

(10) Patent No.: US 8,986,371 B2
(45) Date of Patent: Mar. 24, 2015

(54) METHOD OF TREATING PARAVALVULAR LEAKAGE AFTER PROSTHETIC VALVE IMPLANTATION

(71) Applicant: Medtronic CV Luxembourg S.a.r.l., Luxembourg (LU)

(72) Inventors: Jason Quill, Forest Lake, MN (US); Paul Rothstein, Elk River, MN (US)

(73) Assignee: Medtronic CV Luxembourg S.a.r.l., Luxembourg (LU)

( * ) Notice: Subject to any disclaimer, the term of this patent is extended or adjusted under 35 U.S.C. 154(b) by 333 days.

(21) Appl. No.: 13/736,592

(22) Filed: Jan. 8, 2013

(65) Prior Publication Data
US 2014/0194975 A1 Jul. 10, 2014

(51) Int. Cl.
*A61F 2/24* (2006.01)
*A61B 17/04* (2006.01)

(52) U.S. Cl.
CPC ............. *A61F 2/2427* (2013.01); *A61F 2/2418* (2013.01); *A61B 2017/0437* (2013.01); *A61F 2230/008* (2013.01); *A61F 2220/0075* (2013.01); *A61F 2230/005* (2013.01); *A61F 2230/0054* (2013.01); *A61F 2/2457* (2013.01)
USPC ....................................................... 623/2.11

(58) Field of Classification Search
CPC ... A61F 2/2427; A61F 2/2436; A61F 2/2418; A61F 2/2457; A61F 2/246
See application file for complete search history.

(56) References Cited

U.S. PATENT DOCUMENTS

| 6,797,002 | B2 * | 9/2004 | Spence et al. | 623/2.38 |
|---|---|---|---|---|
| 7,166,126 | B2 * | 1/2007 | Spence et al. | 623/2.36 |
| 7,527,647 | B2 * | 5/2009 | Spence | 623/2.36 |
| 8,100,964 | B2 * | 1/2012 | Spence | 623/2.36 |
| 2003/0083742 | A1 * | 5/2003 | Spence et al. | 623/2.16 |
| 2004/0088047 | A1 * | 5/2004 | Spence et al. | 623/2.36 |
| 2005/0075727 | A1 * | 4/2005 | Wheatley | 623/2.17 |
| 2005/0240202 | A1 * | 10/2005 | Shennib et al. | 606/142 |
| 2007/0050020 | A1 * | 3/2007 | Spence | 623/2.11 |
| 2009/0177278 | A1 * | 7/2009 | Spence | 623/2.37 |
| 2009/0222026 | A1 | 9/2009 | Rothstein et al. | |
| 2010/0023118 | A1 * | 1/2010 | Medlock et al. | 623/2.11 |
| 2012/0022640 | A1 | 1/2012 | Gross et al. | |
| 2012/0095552 | A1 * | 4/2012 | Spence et al. | 623/2.36 |
| 2012/0277853 | A1 | 11/2012 | Rothstein | |
| 2013/0006352 | A1 | 1/2013 | Yaron | |

FOREIGN PATENT DOCUMENTS

WO WO01/00114 1/2001

OTHER PUBLICATIONS

PCT/US2014/010601, PCT Search Report and Written Opinion, Apr. 23, 2014.

* cited by examiner

*Primary Examiner* — Ryan Severson

(57) ABSTRACT

A method for treating paravalvular leakage at a location of a stented prosthetic valve includes the steps of delivering a clip to a location adjacent chordae tendinae of a native valve, and deploying the clip such that the clip captures at least some of the chordae tendinae of the native valve, thereby increasing tension in the captured chordae tendinae. The clip is delivered to the location in a collapsed stated and is released from a sheath convert to an undeflected or relaxed state. After the clip is released from the sheath, the clip is rotated to capture the chordae tendinae. The clip is then released from the delivery system and the delivery system is retracted.

22 Claims, 11 Drawing Sheets

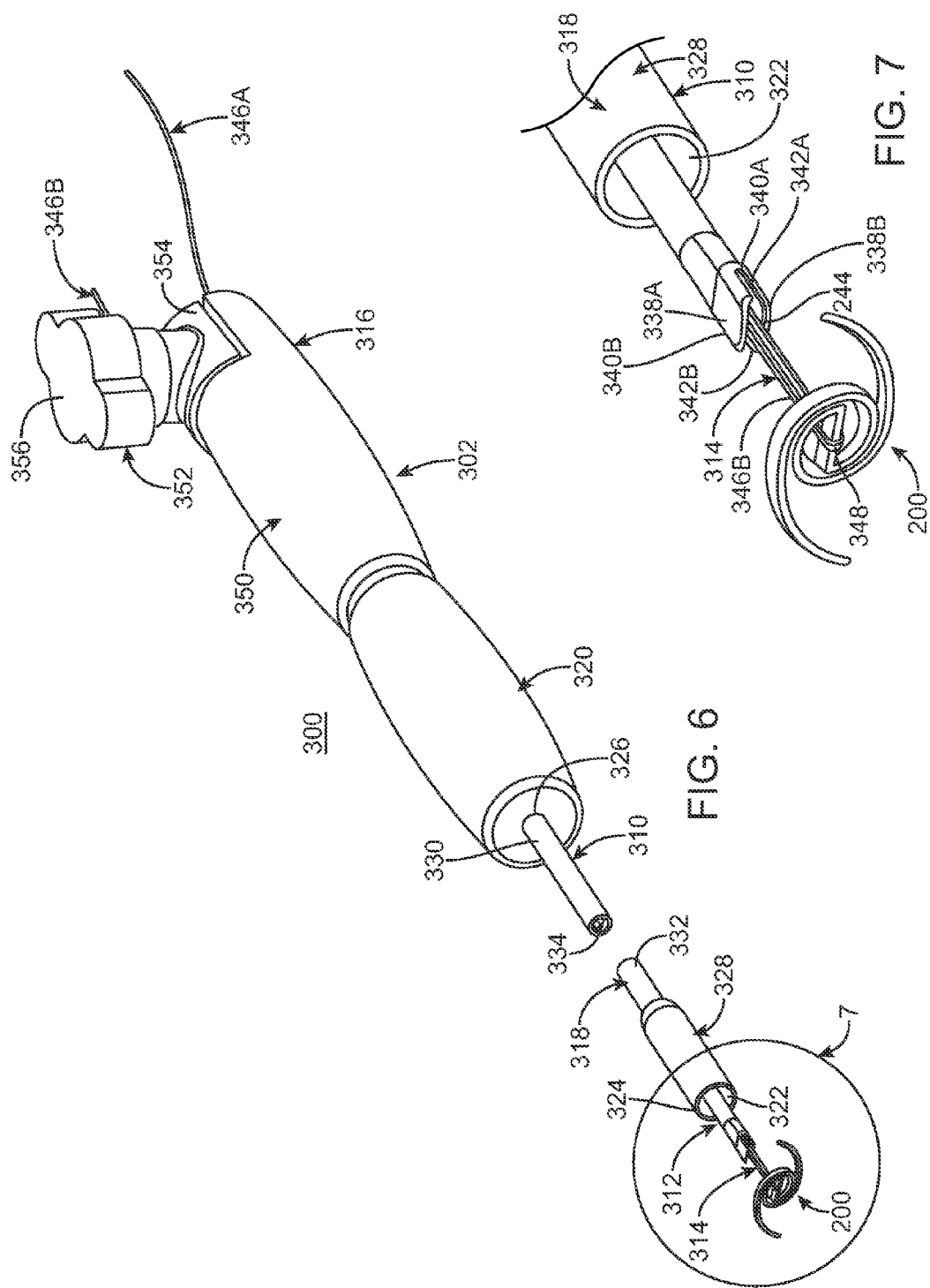

METHOD OF TREATING PARAVALVULAR LEAKAGE AFTER PROSTHETIC VALVE IMPLANTATION

FIELD OF THE INVENTION

The present invention is directed to devices and method for treating paravalvular leakage after implantation of a stented prosthetic valve.

BACKGROUND OF THE INVENTION

A human heart includes two atrio-ventricular valves through which blood flows from the atria to the ventricles, the valves functioning to prevent return of blood to the atrium. The tricuspid valve, also known as the right atrioventricular valve, is a tri-flap valve located between the right atrium and the right ventricle. The mitral valve, also known as the bicuspid or left atrioventricular valve, is a dual-flap valve located between the left atrium (LA) and the left ventricle (LV), and serves to direct oxygenated blood from the lungs through the left side of the heart and into the aorta for distribution to the body. As with other valves of the heart, the mitral valve is a passive structure in that it does not itself expend any energy and does not perform any active contractile function. The mitral valve includes two moveable leaflets that each open and close in response to differential pressures on either side of the valve. Ideally, the leaflets move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with mitral regurgitation or backflow typically having relatively severe physiological consequences to the patient.

Due to the different physical characteristics of the mitral valve as compared to other valves such as the pulmonary valve, percutaneous implantation of a valve in the mitral position has its own unique requirements for valve replacement. There is a continued desire to improve mitral valve replacement devices and procedures to accommodate the structure of the heart, including by providing improved devices and methods for replacing the mitral valve percutaneously.

Replacement of mitral valves is generally performed via surgical technique required open-heart surgery and a cardiopulmonary bypass. Such surgical techniques are not desirable for certain patients. Accordingly, stented prosthetic heart valves have been developed recently to replace damaged heart valves using minimally invasive techniques. Similar transcatheter aortic valve replacement, a stented prosthetic valve for mitral valve replacement includes a prosthetic valve coupled to a stent. The stent is delivered to the site of mitral valve and radially expanded to hold the prosthetic valve in place.

In stented prosthetic aortic valves the stent generally relies of radial forces of the stent to hold the stent and prosthetic valve in place. In some embodiments of stented prosthetic valves for mitral valve replacement, the stent instead uses axial forces for fixation due to the large size of the mitral annulus and the compliance of the left atrium. One exemplary design aims to provide axial fixation by creating tension in the chordae tendinae, thereby holding the inflow section of the stent frame against the mitral annulus. The transition zone between the inflow and outflow sections of the stent frame then provides sealing with the anatomy to prevent paravalvular leakage (PVL) of the transcatheter stented prosthetic mitral valve. FIG. 1 shows a free body diagram showing the forces for such an axial fixation.

However, after delivery and deployment of such a stent prosthetic mitral valve, paravalvular leakage and/or axial motion of the stented prosthetic valve may exist. Currently, there is no treatment for remediation of such axial motion and/or paravalvular leakage after deployment of a stented prosthetic mitral valve. Accordingly, devices and methods are needed for treatment of excessive axial motion and/or paravalvular leakage after implantation of a stented prosthetic mitral valve.

BRIEF SUMMARY OF THE INVENTION

Embodiments hereof relate to a method for treating paravalvular leakage at a location of a stented prosthetic valve includes the steps of delivering a clip to a location adjacent chordae tendinae of a native valve, and deploying the clip such that the clip captures at least some of the chordae tendinae of the native valve, thereby increasing tension in the captured chordae tendinae. The clip is delivered to the location in a collapsed stated and is released from a sheath convert to an undeflected or relaxed state. After the clip is released from the sheath, the clip is rotated to capture the chordae tendinae. The clip is then released from the delivery system and the delivery system is retracted.

Embodiments hereof also relate to a method of implanting a prosthetic valve and treating paravalvular leakage. The method includes the steps of tracking a prosthetic valve delivery system to the native mitral valve in a radially compressed configuration for delivery and deploying the prosthetic valve at the native mitral valve. The method further includes the steps of detecting paravalvular leakage at the prosthetic valve implantation site. After paravalvular leakage has been detected, a clip is delivered to a location adjacent the chordae tendinae of the native mitral valve, and the clip is deployed such that the clip captures at least some of the chordae tendinae of the native mitral valve, thereby increasing tension in the captured chordae tendinae. The prosthetic valve includes a valve prosthesis having a tubular stent, a prosthetic valve component disposed within and secured to the stent, and at least two support arms coupled to and distally extending from a distal end of the stent when the stent is in the radially compressed configuration. The prosthetic valve is deployed by retracting an outer sheath of the prosthetic valve delivery system to expose the support arms, wherein each support arm bends radially outward and then towards an outer surface of the stent, and further retracting the outer sheath to expose the stent, thereby allowing the stent to self-expand into the deployed configuration. The clip is deployed by releasing the clip from a sheath such that the clip converts from a collapsed state to an undeflected state and rotating the clip in the undeflected state adjacent the chordate such that the clip captures at least some of the chordae tendinae as the clip is being rotated. The clip may then be released from the delivery device and the delivery device may be retracted.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 6 is a perspective view of a clip delivery system including the clip of FIG. 4 and a clip delivery device.

FIG. 7 is an enlarged, perspective view of a distal portion of the system of FIG. 6.

DETAILED DESCRIPTION OF THE INVENTION

Figure 1:
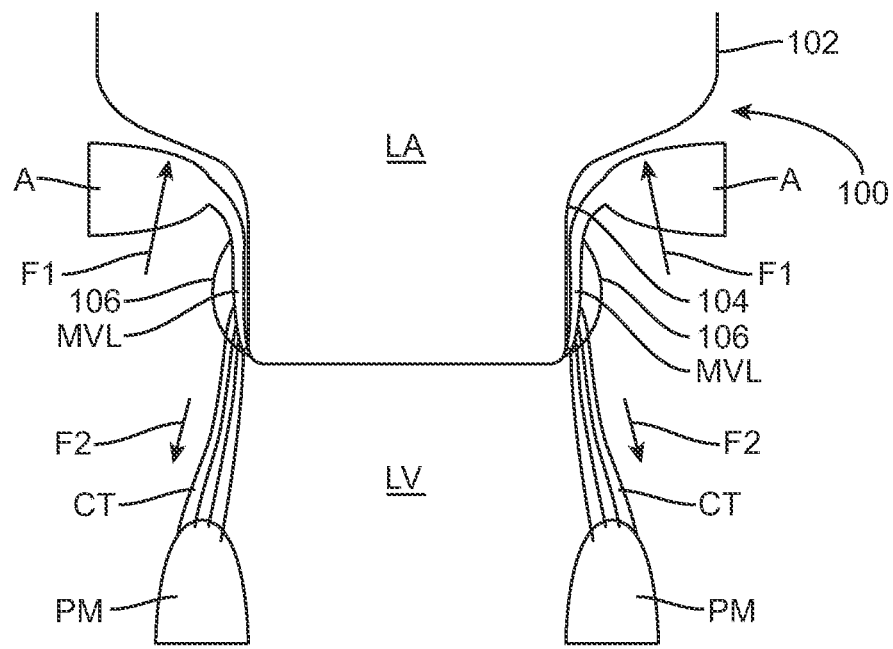
FIG. 1 is schematic free body diagram showing forces of an implanted stented prosthetic mitral valve.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. In addition, as used herein, the terms "outward" or "outwardly" refer to a position radially away from a longitudinal axis of the stent and the terms "backward" or "backwardly" refer to the relative transition from a distal position to a proximal position.

The following detailed description is merely exemplary in nature and is not intended to limit the invention or the application and uses of the invention. Although the description of the invention is in the context of treatment of heart valves such as the mitral valve, the invention may also be used in any other body passageways where it is deemed useful. Furthermore, there is no intention to be bound by any expressed or implied theory presented in the preceding technical field, background, brief summary or the following detailed description.

Embodiments hereof are related to devices and methods for treating paravalvular leakage and/or prosthesis movement after a stented valve prosthesis has been implanted at a mitral valve in the heart that lies between the left atrium LA and the left ventricle LV. As explained above and shown in FIGS. 1 and 2, a stented valve prosthesis 100 is installed at the site of a mitral valve between the left atrium LA and the left ventricle LV. The stented valve prosthesis 100 includes a proximal or atrial or inflow section 102, a distal or ventricular or outflow section 104, and support arms 106. When installed, each support arm 102 captures one of the two native mitral valve leaflets MVL between the support arm 106 and an exterior surface of the outflow section 104. Chordae tendinae CT (sometimes referred to as "heart strings") are cord-like tendons that connect the papillary muscles PM to the mitral valve leaflets MVL. Thus, as the mitral valve leaflets MVL are bent outwards or held apart by outflow section 104 and support arms 106 of the stent valve prosthesis 100, the chordae tendinae CT are placed in tension. This tension creates opposing axial forces F1 and F2 acting against the stented valve prosthesis 100 to the keep the stented valve prosthesis 100 in place.

Figure 2:
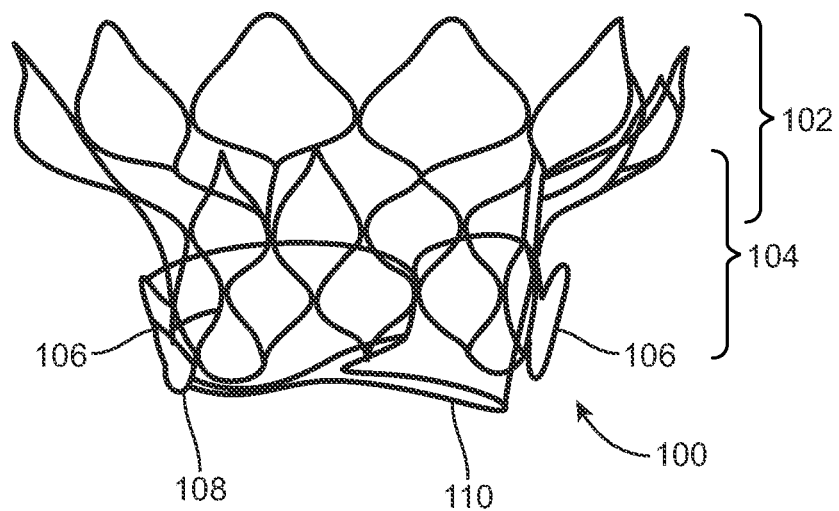
FIG. 2 is a schematic illustration of an exemplary stented prosthetic valve, wherein the stent is in an expanded or deployed configuration.

FIG. 2 shows the stented valve prosthesis 100 in its expanded configuration without the valve component shown. Thus, FIG. 2 shows the framework or stent 101, including the inflow section 102 with a larger diameter than the outflow section 104. When placed at a native mitral valve target site, outflow section 104 extends into the left ventricle and inflow section 102 extends into the left atrium. Each section of stent 101, i.e., outflow section 104 and/or inflow section 102, may be designed with a number of different configurations and sizes to meet the different requirements of the locations in which it may be implanted. Each section of stent framework 101, i.e., outflow section 104 and/or inflow section 102, may have the same or different cross-section which may be for example circular, ellipsoidal, rectangular, hexagonal, square, or other polygonal shape, although at present it is believed that circular or ellipsoidal may be preferable when the valve prosthesis is being provided for replacement of the mitral valve. Support arms or positioning elements 106 bend or rotate more than ninety degrees with respect to its compressed, delivery configuration during deployment of stented valve prosthesis 100. In one embodiment, each support arm 106 rotates between 135 degrees and 180 degrees during deployment of stented valve prosthesis 100. In the radially compressed or delivery configuration, each support arm 106 extends distally from a distal end 108 of stent 101. When released from a delivery sheath, each support arm 106 gradually bends outwardly and then towards an outer surface of the delivery device or stent until it reaches its deployed configuration of FIG. 2 in which each support arm 106 extends proximally from distal end 108 of stent 101. The stent 101 shown in FIGS. 1 and 2 are exemplary in nature. Accordingly, other stents for use in supporting a valve component may be used. For example, and not by way of limitation, stents and stented valve prostheses shown and described in U.S. patent application Ser. No. 13/572,842, filed Aug. 13, 2012, which is incorporated by reference herein in its entirety. Other stented valve prostheses, such as those described in U.S. Patent Application Publication Nos. 2011/0137397 to Chae et al., 2009/0276040 to Rowe et al., 2009/0005863 to Goetz et al., and 2010/0217382 to Chau et al., each of which is hereby incorporated by reference herein in its entirety.

In embodiments hereof, stent 101 may be made from stainless steel, a pseudo-elastic metal such as a nickel titanium alloy or Nitinol, or a so-called super alloy, which may have a base metal of nickel, cobalt, chromium, or other metal. Stent 101 is self-expanding to return to an expanded or deployed configuration from a compressed or constricted delivery configuration. "Self-expanding" as used herein means that stent 101 has a mechanical memory to return to the expanded or deployed configuration. Mechanical memory may be imparted to the wire or tubular structure that forms stent 101 by thermal treatment to achieve a spring temper in stainless steel, for example, or to set a shape memory in a susceptible metal alloy, such as nitinol, or a polymer, such as any of the polymers disclosed in U.S. Pat. Appl. Pub. No. 2004/0111111 to Lin, which is incorporated by reference herein in its entirety. For self-expanding stent structures, one example of a delivery system that can be used includes a catheter with a retractable sheath that covers and compresses the stent and its associated valve structure until it is to be deployed, at which point the sheath can be retracted to allow the stent frame to assume its expanded or deployed configuration. Further details of such a delivery process for delivering stented valve prostheses as described herein are discussed in further detail below.

Figure 3:
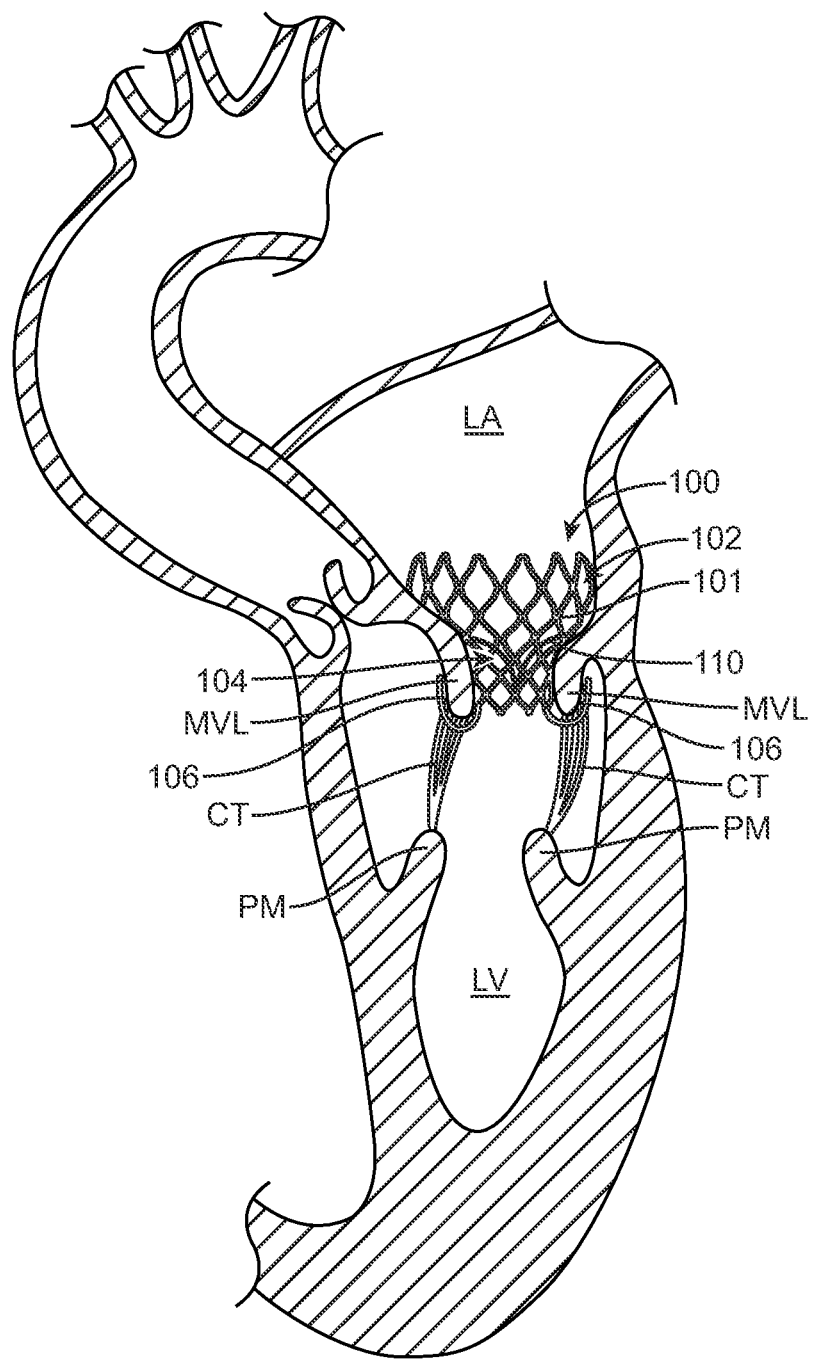
FIG. 3 is a side view illustration of the exemplary stented prosthetic valve of FIG. 2, wherein the stent is in an expanded or deployed configuration and positioned at a mitral valve of a heart.

FIG. 3 shows stented valve prosthesis 100 deployed within a heart at the site of the mitral valve. As can be seen in FIG. 3, inflow section 102 is extends into the let atrium LA, outflow section 104 extends into the left ventricle LV, and support arms 106 capture the mitral valve leaflets MVL between the support arms 106 and an outer surface of outflow section 104 of valve prosthesis 100. FIG. 3 also shows a prosthetic valve component 110 of stent valve prosthesis 100 disposed within the interior of stent 101. Prosthetic valve component 110 functions to replace the function of the mitral valve leaflets MVL, as known in the art. Prosthetic valve component 110 includes valve leaflets that may form a bicuspid, tricuspid, or tubular replacement valve. Prosthetic valve component 110 is sutured or otherwise securely and sealingly attached to the interior surface of stent 101 and/or graft material (not shown) enclosing or lining stent 101 as known to one of ordinary skill in the art of prosthetic tissue valve construction. Leaflets of prosthetic valve component 110 may be made of pericardial material or other materials. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets of prosthetic valve component 110 include DACRON® polyester commercially available from Invista North America S.A.R.L. of Wilmington, Del., other cloth materials, nylon blends, polymeric materials, and vacuum deposition nitinol fabricated materials. One polymeric material from which the leaflets can be made is an ultra high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

As explained above, when stented prosthetic valve 100 is deployed within the mitral valve as shown in FIG. 3, there may be some paravalvular leakage due to axial motion if the tension forces described with respect to FIG. 1 are not sufficient. Such paravalvular leakage may be detected after installation of stented prosthetic valve 100 described above or other similar stented prosthetic valves that rely on chordal tension for axial fixation of the stented prosthetic valve. Such paravalvular leakage may be detected and located using any of a number of visualization techniques, such as intravascular ultrasound (IVUS), transesophageal echocardiography (TEE), intracardiac echocardiography (ICE), angiographic ventriculogram, or other available techniques known to those skilled in the art.

Figure 4:
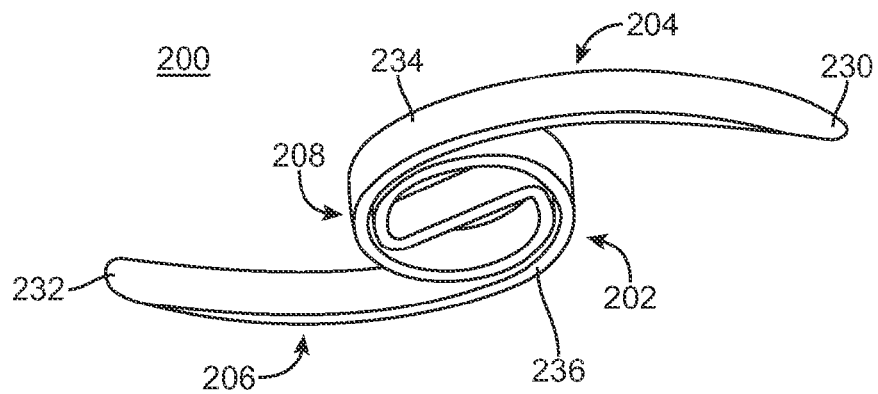
FIG. 4 illustrates a perspective view of an exemplary spiral clip according to an embodiment hereof.
Figure 5:
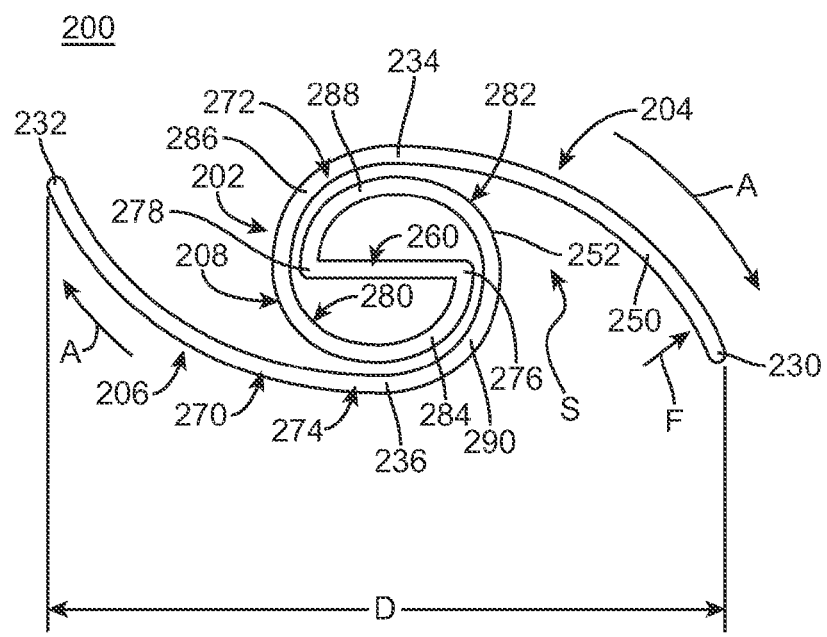
FIG. 5 is a top view of the clip of FIG. 4.

FIGS. 4 and 5 illustrate an embodiment of a clip 200 which may be used to provide additional tensioning of the chordae tendinae after installation of a stented prosthetic valve. Clip 200 may be similar to the clips described in commonly assigned U.S. Patent Application Publication No. 2009/0222026 A1, the entirety of which is incorporated by reference herein (hereinafter referred to as "the '026 publication"). However, while the clips of the '026 publication is used to proximate tissue for example closing an internal tissue defect, clip 200 of the present application for wrapping around the chordae tendinae connected to one of the leaflets of a valve. One particular difference between the clips of the '026 publication and clip 200 hereof is that the tips of clip 200 are rounded, as described in more detail below. In other aspects, any of the embodiments of the clips of the '026 publication and delivery devices therefore may be used as described herein.

Clip 200 is shown in a relaxed or undeflected state in FIGS. 3 and 4. During use, and as described below, the clip 200 is deflectable or collapsible from the undeflected state of FIGS. 3 and 4 to a collapsed state, and will self-revert from the collapsed state to or toward the undeflected state. With this in mind, in at least the undeflected state, clip 200 includes or defines a center portion 202, a first leg or prong 204, and a second leg or prong 206. Details on the components are provided below. In general terms, however, center portion 202 has a perimeter 208 defining a circular or circle-like shape. The legs 204, 206 project outwardly relative to the perimeter 208, with the first leg 204 terminating at a tip 230, and the second leg 206 terminating at a tip 232. In this regard, the legs 204, 206 extend in or with an identical wind direction, such that the clip 200 has, in some embodiments, a hurricane-like shape (as best reflected by the top plan view of FIG. 5).

The wind direction associated with each of the legs 204, 206 is either clockwise or counterclockwise relative to the circle-like shape of the perimeter 208. The perimeter 208 may or may not be continuous, and may or may not reflect a true circle; relative to a two-dimensional top (or bottom) plan view, however, the perimeter 208 of the center portion 202 establishes a basis from which clock-type directional attributes (e.g., wind direction) can be identified. For example, the first leg 204 extends from the perimeter 208 at a point of departure 234, terminating at the tip 230. The point of departure 234 can be defined as a point along the leg 204 at which a lateral spacing between the leg 204 and the perimeter 208 begins to increase. By way of clarification, the point of departure 234 is at approximately a 12 o'clock position of the perimeter 208 relative to the orientation of FIG. 5. With these conventions in mind, FIG. 5 depicts the first leg 204 as establishing a wind direction (represented by the arrow "A") that is clockwise. Extension of the second leg 206 relative to the perimeter 208 from a point of departure 236 similarly defines the same clockwise wind direction A. Alternatively, the wind direction established by both of the legs 204, 206 can be counterclockwise.

In some embodiments, the legs 204, 206 can have an identical construction/dimensions. Thus, the legs 204, 206 can define an identical curvature in extension from the perimeter 208. Alternatively, the legs 204, 206 can have differing dimensions and/or curvatures. Similarly, one or both of the legs 204, 206 can have a linear segment or be entirely linear (i.e., extend tangentially from the perimeter 208). Regardless, the wind direction A of the legs 204, 206 are identical.

As best shown in FIG. 5, the legs 204, 206 are in some embodiments, positioned opposite one another relative to the perimeter 208. Thus, the point of departure 234 of the first leg 204 is opposite the point of departure 236 of the second leg 206. As explained in the '026 publication, clip 200 is symmetrical. However, in other embodiments, clip 200 may be asymmetrical. Further, in other embodiments, three or more legs may be provided and may or may not be equidistantly spaced about the perimeter 208.

Clip 200 is constructed such that the legs 204, 206 elastically resist movement away from the perimeter 208, both axially and radially relative to the perimeter 208. For example, a radial or lateral spacing S is defined between an inner surface 250 of the first leg 204 and a region 252 of the perimeter 208 closest to the inner surface 250. As a point of reference, relative to any one point along the inner surface 250, a minimum lateral spacing S is established relative to the closest, adjacent point along the perimeter 208, with this minimum lateral spacing S increasing from the point of departure 234 to the tip 230. With this in mind, the affinity of the first leg 204 to resist laterally outward movement relative to the perimeter 208 is characterized by the leg resisting a force tending to increase the lateral spacing S. In other words, a force (generically represented by an arrow "F" in FIG. 5) exerted or experienced along the inner surface 250 tends to cause the first leg 204 to move in a direction opposite the wind direction A. Construction of the clip 200 causes the first leg 204 to resist this unwinding-type force. Instead, the first leg 204 (as well as the second leg 206) slightly deflects in response to the force F, causing material (such as tissue) within the lateral spacing S to gather or pinch between the inner surface 250 and the region 252 of the perimeter 208 as described below.

In the undeflected state of FIG. 5, a maximum outer dimension D of the clip 200 is defined as a linear distance between the first and second tips 230, 232. The outer dimension D for a clip 200 used for chordal tensioning at the site of a stented prosthetic valve may be in the range of 3-10 mm. However, other smaller or larger sized may be utilized. As explained in the '026 publication, clip 200 is collapsible from the undeflected state of FIG. 5 to a collapsed state in which the maximum dimension D is greatly reduced such that the collapsed clip 200 is more readily delivered to a confined site, such as via a catheter or similar body. Further, upon removal of the force(s) otherwise causing the clip 200 to remain in the collapsed state, the clip 200 self-reverts back to the undeflected state of FIGS. 4 and 5. An ability of the clip 200 to self-revert from a collapsed state to the undeflected state is provided, in some embodiments, by forming the clip 200 from an elastic material, such as stainless steel, and in other embodiments, a super elastic material such as a shape memory alloy, for example Nitinol.

In the embodiment shown in FIGS. 4 and 5, the clip 200 further includes or forms a linear cross-member 260 extending within the circular-like perimeter 208. The cross-member 260 can assume a variety of forms, and in some embodiments is configured for interface with a delivery device to facilitate transfer of a torque or rotational force applied to the cross-member 260 to the center portion 202 and the legs 204, 206.

In some embodiments, the clip 200 is formed by a single wire 270 the ends or tips 230, 232 of which are rounded so as not to pierce tissue. The wire 270 is partially wound onto itself during manufacture to define a cross-member segment (i.e., the cross-member 260), a first section 272, and a second section 274. The cross-member 260 has or is defined by opposing, first and second ends 276, 278. The first section 272 extends from the first end 276 and is wound (in a single wind direction, for example clockwise relative to FIG. 5) to define a first segment 280 and the first leg 204. More particularly, the first segment 280 extends from the first end 276 of the cross-member 260 and forms a portion of the perimeter 208. The first leg 204 extends from the first segment 280. With this in mind, the first segment 280 has, in some embodiments, a relatively uniform radius of curvature (slightly increasing from the first end 276), with this radius of curvature being less than a radius of curvature defined by the first leg 204. As a point of reference, while the point of departure 234 has been designated relative to the perimeter 208, the wound form of the first section 272 also identifies the point of departure 234 as being a location along a length of the wire 270 at which the wound radius of curvature significantly increases (e.g., greater than 25 percent). The second section 274 extends from the second end 278 in a similar manner (and identical wind direction), defining a second segment 282 and the second leg 206. In some embodiments, the first and second sections 272, 274 are identical. Thus, a radius of curvature of the second segment 282 is less than a radius of curvature of the second leg 206, with the point of departure 236 being defined as a location along a length of the wire 270 where the radius of curvature significantly increases.

Winding of the first and second segments 280, 282 is such that the segments 280, 282 partially circumferentially overlap one another in a spiral-like manner. For example, the first segment 280 can be defined as having a leading region 284 and a trailing region 286. Similarly, the second segment 282 can be defined as having a leading region 288 and a trailing region 290. As shown, in the undeflected state, a portion of the trailing region 286 of the first segment 280 circumferentially overlaps (i.e., is radially outside of) a portion of the leading region 288 of the second segment 272. Similarly, a portion of the trailing region 290 of the second segment 282 circumferentially overlaps a portion of the leading region 284 of the first segment 280. With this construction, as the first leg 204 is forced away from the perimeter 208 (i.e., unwound), a slight circumferential gap will be formed (or an existing gap will be enlarged) between the trailing region 286 of the first segment 280 and the leading region 288 of the second segment 282. Similarly, a circumferential gap is created and/or expanded between the trailing region 290 of the second segment 282 and the leading region 284 of the first segment 280 with forced movement of the second leg 206 away from the perimeter 208. As described below, these gaps effectively serve as pathways for forced gathering of chordae tendinae within the center portion 202 in connection with a chordae tendinae tensioning procedure.

While a particular clip 200 has been described above, it would be understood that other clips having different constructions, including but not limited to other embodiments of the clip of the '026 publication, may be utilized in the method described herein. Further, different delivery and deployed devices for such clips may be utilized. FIGS. 6 and 7 illustrate a particular example of a system 300 for delivering the clip 200 to, and manipulating the clip 200 at, an internal region of a patient, as described in the '026 publication with respect to FIGS. 6-9 thereof. System 300 includes a delivery device 302 which together with the clip 200 defines system 300. Delivery device 302 is akin to a catheter-type device, and is configured to selectively maintain the clip 200 in a collapsed state (it being understood that the clip 200 is shown in the undeflected state in FIG. 6), as well as placement and manipulation of the clip 200 during use.

In some embodiments, the delivery device 302 includes a sheath assembly 210, a retainer 312, an optional tether 314, and a handle assembly 316. Details on the components 310-316 are provided in the '026 publication in FIGS. 6A and 6B, wherein the reference numerals "2xx" in the '026 publication are reference numerals "3xx" in FIGS. 6 and 7 of the present application. Accordingly, the details of system 300 are not repeated herein, but instead are incorporated by reference from the '026 publication.

However, in general terms, the sheath assembly 310 includes a sheath 318 sized to slidably receive the clip 200. The retainer 312 is slidably disposed within the sheath 318 and is configured to selectively retain the clip 200, for example in conjunction with the tether 314. The handle assembly 316 maintains the retainer 312 and the tether 314 relative to the sheath assembly 310, and facilitates transmission of a user-applied force onto the retainer 312, and thus onto the clip 200 when the clip 200 is otherwise engaged with the retainer 312. With this configuration, the retainer 312 and the tether 314 retain the clip 200 both within and distal the sheath 318. Further, the handle assembly 316 allows a user to manipulate the clip 200 in a desired fashion (e.g., rotate) as described below.

The sheath assembly 310 includes the sheath 318 and a hub 320. The hub 320 is mounted to the sheath 318 and provides a user with a convenient surface for manipulating the sheath 318 in a desired fashion. The sheath 318 can be akin to a catheter, sized for insertion into a blood vessel or other bodily lumen. The sheath 318 is thus a tubular body defining a lumen 322 extending from a distal end 324 to a proximal end 326. The lumen 322 is open at the distal end 324 and is optionally open at the proximal end 326 for receiving the retainer 312. Alternatively, a radial port can be formed for accessing the lumen 322. In some configurations, a distal section 328 of the sheath 318 has a slightly enlarged diameter as compared to a proximal section 330 (and in some embodiments as compared to an intermediate section 332). Regardless, a diameter of the lumen 322 at the distal section 328 is sized to force and maintain the clip 200 at a desired outer dimension (i.e., collapsed state) appropriate for advancement through the patient's vasculature (or other pathway) as described below. Thus, at least the distal section 328 of the sheath 318 exhibits sufficient circumferential structural strength or integrity to maintain the clip 200 in the desired collapsed state without failure.

The hub 320 is mounted to the proximal end 326 of the sheath 318, and can assume a variety of forms and sizes. In general terms, the hub 320 serves as a handle or grip for a user to easily grasp, facilitating user manipulation of the sheath 318 (e.g., to effectuate distal or proximal sliding movement of the sheath 318 relative to the retainer 312). Thus, the hub 320 can form a longitudinal bore (not shown) through which the retainer 312 is slidably received.

The retainer 312 is an elongated body, at least a portion of which is sized to be slidably received within the lumen 322 of the sheath 318. In some configurations, the retainer 312 is tubular, forming a central passage 334 through which the tether 314 is received. With specific reference to FIG. 7, a distal region 336 of the retainer 312 is configured to selectively engage the clip 200. For example, in some embodiments, the distal region 336 is partially flattened (relative to an initially round, circular shape in transverse cross-section) to define opposing side walls 338a, 338b, and opposing end walls 340a, 340b. Slots 342a, 342b (the slot 342b being partially visible in FIG. 7) are formed in the opposing end walls 340a, 340b, respectively. The slots 342a, 342b are axially open at a distal end 344 of the distal region 336, and extend through a thickness of the corresponding end wall 340a or 340b. Thus, where the retainer 312 is formed as a tubular body, the slots 342a, 342b are open to the passageway 334. With this construction, the slots 342a, 342b are sized to receive a corresponding portion of the clip 200 as described below. The slots 342a, 342b are but one acceptable configuration for providing desired selective connection of the retainer 312 with the clip 200. A wide variety of other constructions are also acceptable, so long as a sufficient connection with the clip 200 is achieved for transmitting a torque from the retainer 312 onto the clip 200.

The optional tether 314 is, in some embodiments, a continuous suture or other thread extending through the passageway 334 of the retainer 312 (and thus through the sheath 318). As described below, the tether 314 selectively engages the clip 200, for example by wrapping about a corresponding segment of the clip 200. Thus, in the partially assembled state of the system 300 in FIGS. 6 and 7, the tether 314 is arranged to effectively define first and second sections 346a, 346b that extend through the retainer 312 and the handle assembly 316, interconnected by a wrapped portion 348 (FIG. 7) that is threaded about a component of the clip 200.

The handle assembly 316 includes a handle 350 and a locking device 352. The handle 350 is mounted to a proximal end (not shown) of the retainer 312, and provides a grip surface for a user to apply a torque to the retainer 312. With this configuration, then, the retainer 312 extends through the hub 320 that is otherwise mounted to the sheath 318. The locking device 352 is optionally provided, and is movably associated with the handle 350. In particular, the locking device 352 is configured to selectively capture or lock the tether 314 and includes, in some embodiments, a locking plate 354 and an actuator 356. More particularly, the locking device 352 is constructed and assembled to the handle 350 such that the locking plate 354 is moved relative to the handle 350 via operation (e.g., rotation) of the actuator 356, facilitating a tight engagement of the tether 314 between the locking plate 354 and the handle 350. Operation of the actuator 356 in an opposite direction releases the locking plate 354 relative to the handle 350, and thus allows the tether 314 to be freely manipulated relative to other components of the delivery device 302. Alternatively, the locking device 352 can assume a wide variety of other forms appropriate for locking and releasing the tether 314. Further, with embodiments in which the tether 314 is eliminated, the locking device 352 can also be eliminated.

Upon final assembly of the delivery device 302, the retainer 312 is slidably disposed within the sheath 318. Further, the retainer 312 extends through the hub 320, such that the hub 320, as well as the sheath 318, is longitudinally slidable over the retainer 312 (and thus the retainer 312 is axially slidable within the sheath 318 and the hub 320). Prior to assembly of the clip 200 to the delivery device 302, the tether 314 is not fully disposed within the retainer 312 in the manner reflected in FIGS. 6 and 7. For example, while the first section 346a may be loaded or threaded through the retainer 312 and the handle 350, an entirety of the second section 346b extends distal the distal end 344 of the retainer 312 for subsequent assembly about the clip 200 as described in the '026 publication.

Figure 8:
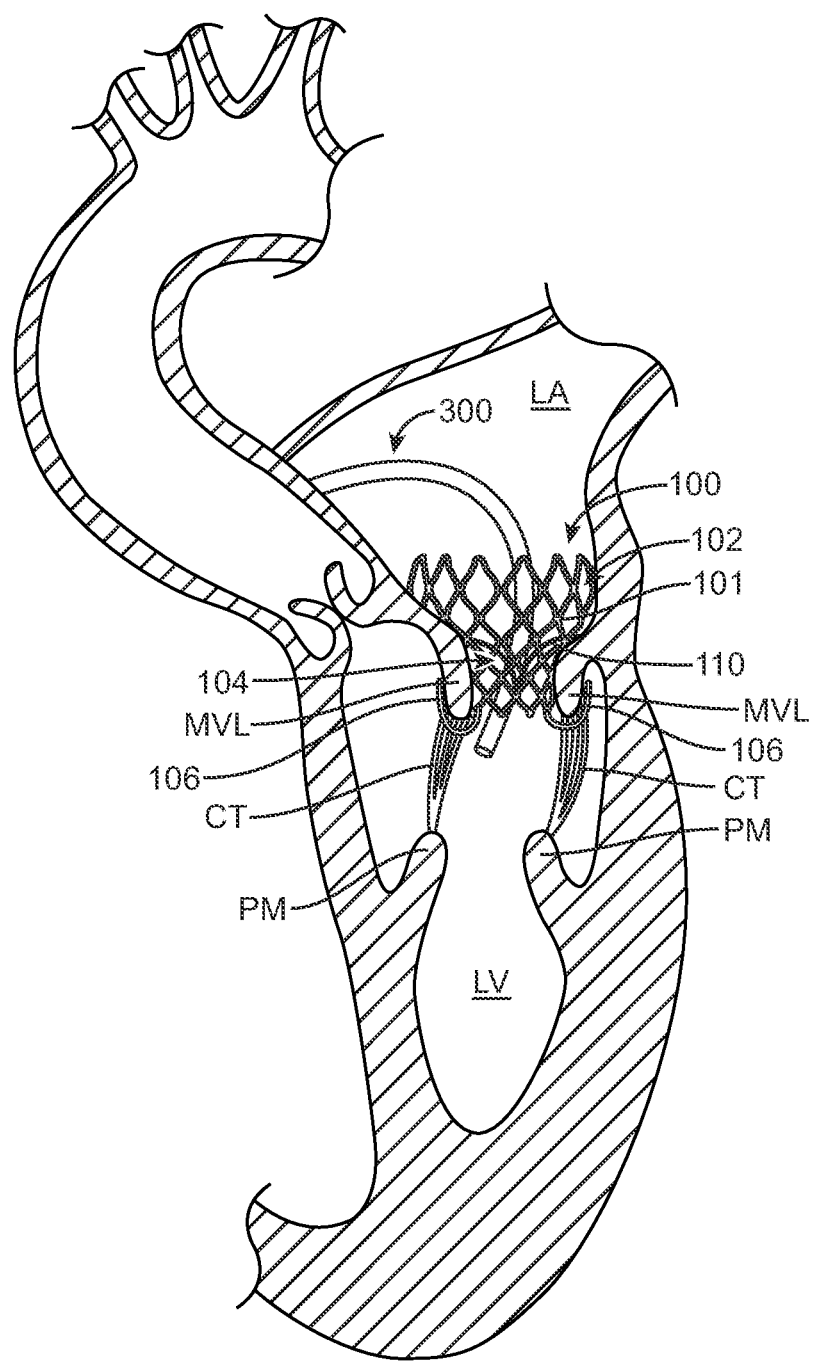
FIGS. 8-14 illustrate a method of implanting a stented valve prosthesis at a mitral valve target location within a heart, checking the target location for paravalvular leakage after implantation of the stented valve prosthesis, and implanting a clip around chordae tendinae of the mitral valve leaflets for treatment of paravalvular leakage after stented prosthetic valve implantation.

FIGS. 8-14 show a method for treating paravalvular leakage at a location where a stented valve prosthesis has been implanted. The method may include the step of implanting the stented valve prosthesis which may be performed as described in U.S. patent application Ser. No. 13/572,842, filed Aug. 13, 2012, which is incorporated by reference herein in its entirety, or other methods known to those skilled in the art. However, the method is not necessarily performed at the same time as the implantation of the stented valve prosthesis. The stented valve prosthesis may be stented valve prosthesis 100 of described above, or any other suitable stented valve prosthesis. The stented valve prosthesis 100 may be one that relies at least partially on axial forces to maintain stented valve prosthesis 100 in place, as described above. FIG. 8 shows stented valve prosthesis 100 implanted at the location of the mitral valve between the left atrium LA and the left ventrical LV.

Figure 14:
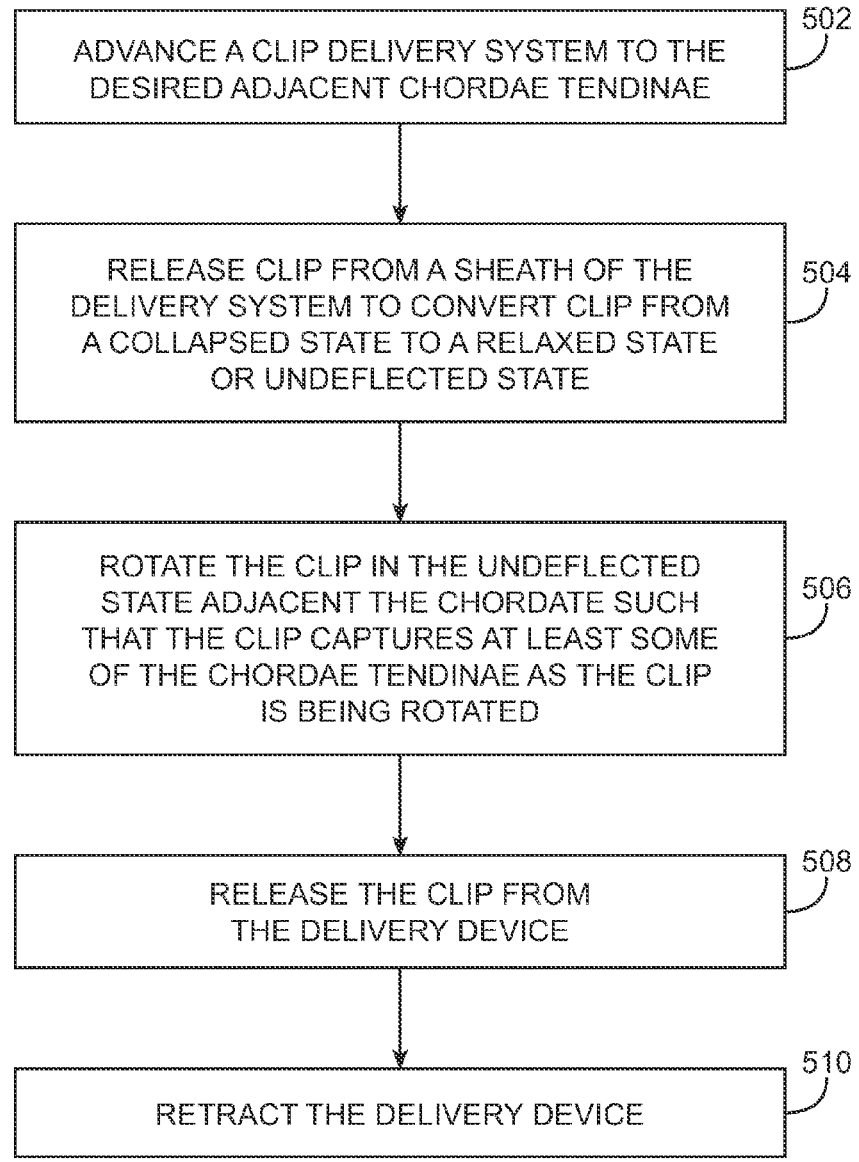

Step 502 of FIG. 14 is to advance clip delivery system 300 to the desired site, as shown in FIG. 8. In this particular embodiment, the location is the left ventricle LV. In the embodiment shown in FIG. 8, system 300 is advanced via a transeptal approach. In particular, and incision is made in the atrial portion of the septum to allow access into the left atrium from the right atrium, such as via the inferior or superior vena cava. In other embodiments, a transatrial approach (not shown) can be used wherein an incision is made through an atrial wall of the left atrium LA, for example by an incision through the chest. Other approaches, such as an antegrade approach via the aorta and through the aortic valve or a transapical approach in which access is made to the left ventricle LV via the heart apex, as known to those skilled in the art, may also be used.

Figure 9:
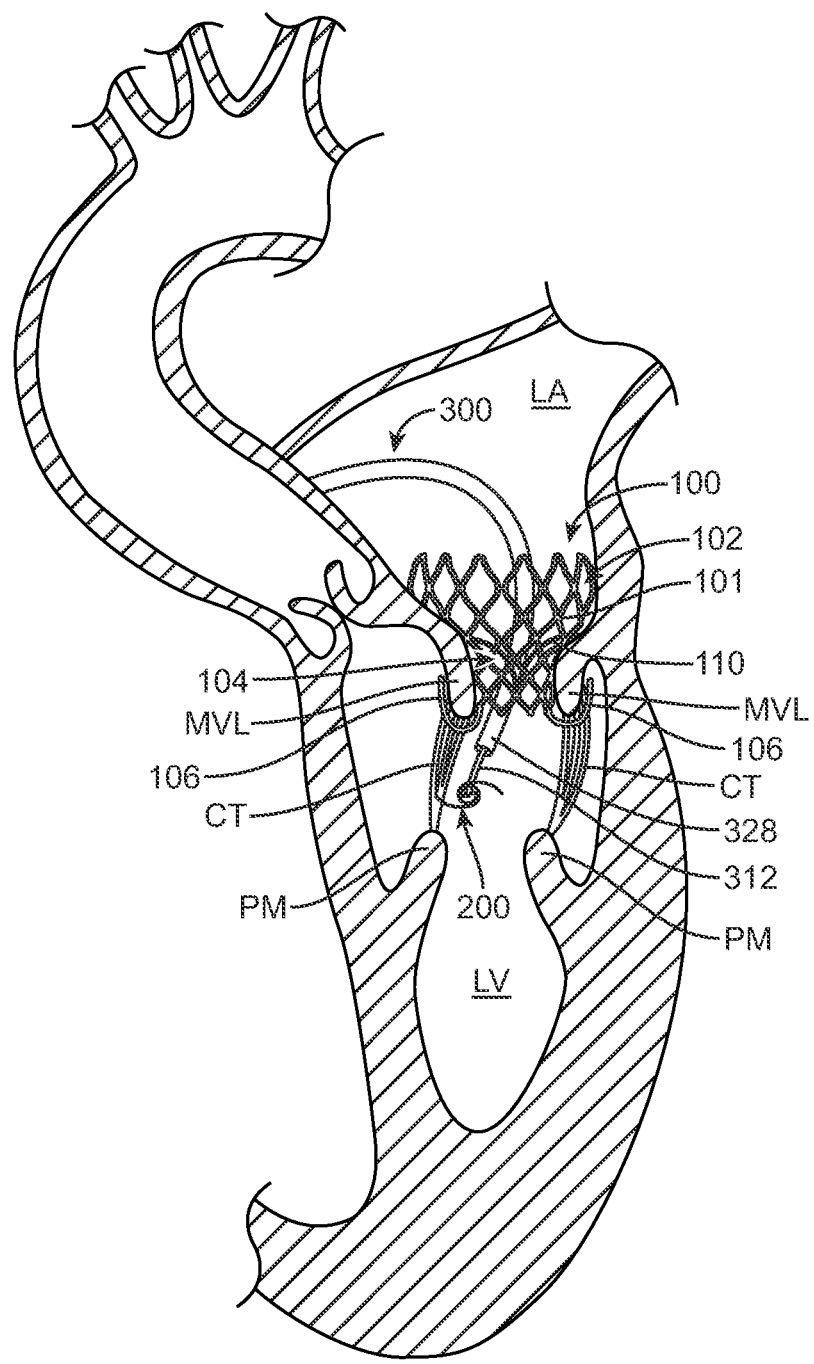

With system 300 in place such that distal section 328 of sheath 318 is positioned adjacent the chordae tendinae CT to which the clip 200 is to be applied, as shown in FIG. 8, delivery device 302 is operated to position the clip 200, and thus the distal region 326 of the retainer 312, distal the distal end 324 of sheath 318, as shown in FIG. 9 and step 504 of FIG. 14. For example, and as described in the '026 application, hub 320 is moved proximally toward handle 350, such that clip 200 is distally beyond or outside of the sheath 318. To assist in deploying clip 200 from the sheath 318, the retainer 312, and thus the clip 200, can be rotated (e.g., approximately) 180°). Regardless, once free of the confines of the sheath 318, clip 200 will self-revert to the undeflected state. If it is determined that the clip 200 is not positioned at a desired location relative to the chordae tendinae CT, the clip 200 can be collapsed back into the sheath 318, and the sheath 318 then re-located as desired.

Figure 10:
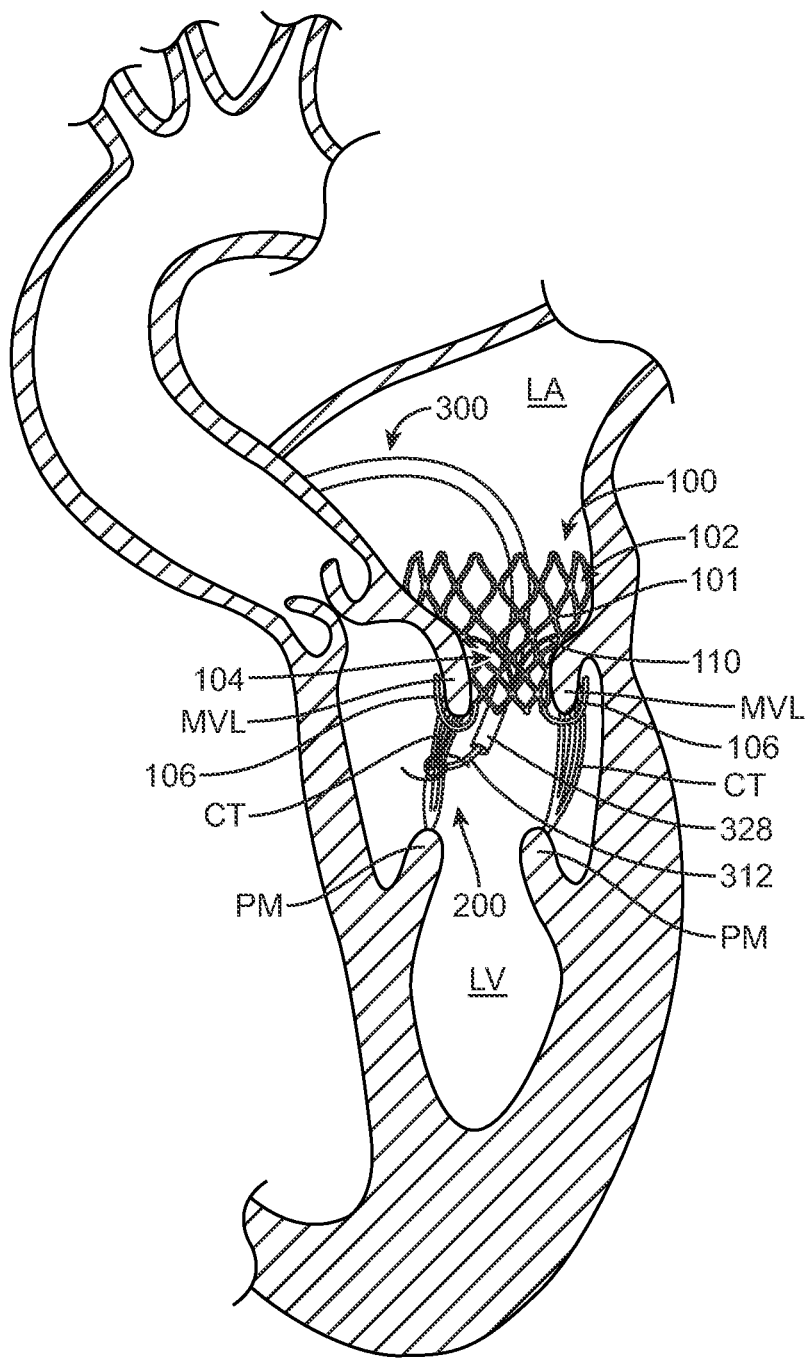
Figure 11:
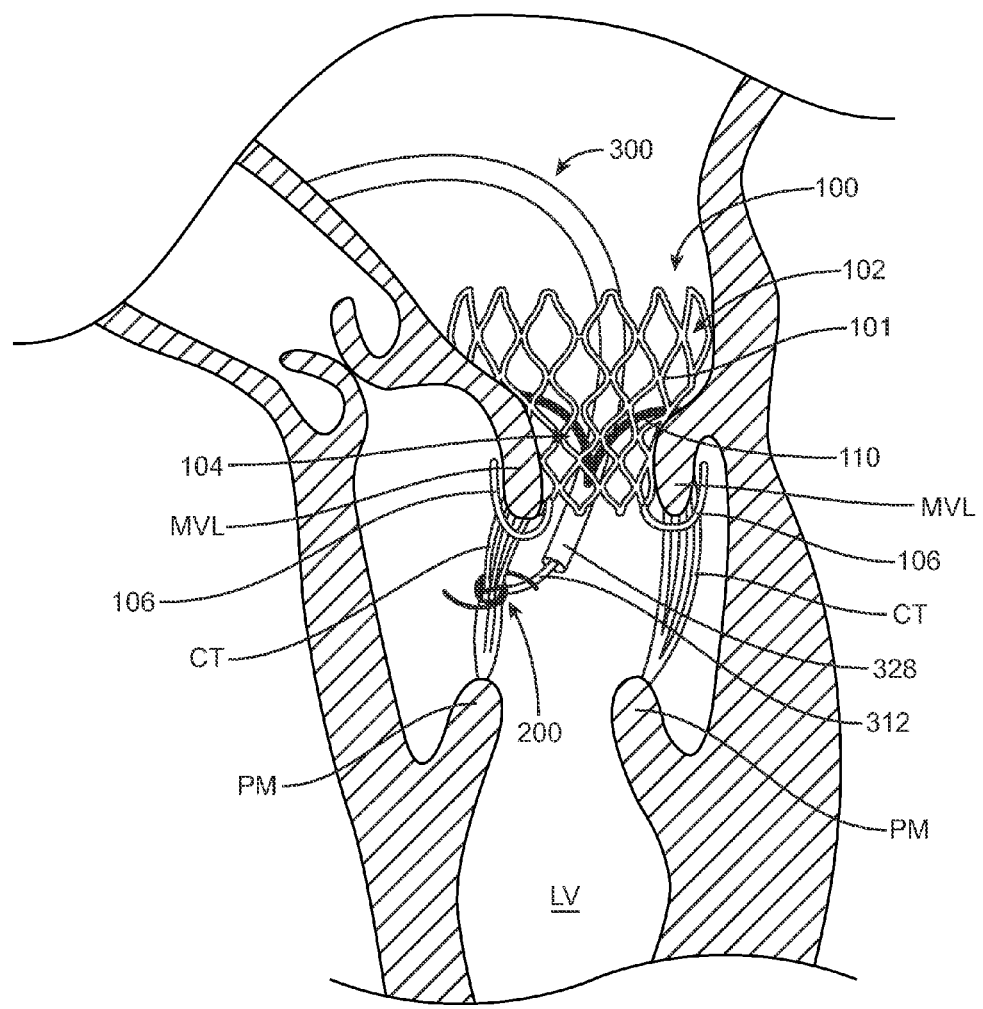

Once deployed from the sheath 318, clip 200 is rotated via rotation of handle 350 and thus the retainer 312 to capture the chordae tendinae CT attached to one of the mitral valve leaflets MVL, as shown in FIGS. 10 and 11, and step 506 of FIG. 14. In particular, a user-applied torque at handle 350 is transmitted to clip 300 due to continued engagement with the distal region 336. Rotation of the clip 200 in the wind direction of the legs 204, 206 causes the chordae tendinae CT to be captured by legs 204 and gathered within the center portion 202. By gathering or bunching the chordae tendinae CT within clip 200, the distance required to be travelled by the chordae tendinae CT between the mitral valve leaflet MVL and the papillary muscle PM is effectively lengthened. However, instead of the chordae tendinae CT lengthening, additional tension is created in the chordae tendinae CT between the respective mitral valve leaflet MVL and the papillary muscle PM. Such additional tension provides additional support for the stented prosthetic valve 100 such that movement of stented prosthetic valve 100 is minimized, thereby minimizing the risk of paravalvular leakage around stented prosthetic valve 100 due to such movement.

Figure 12:
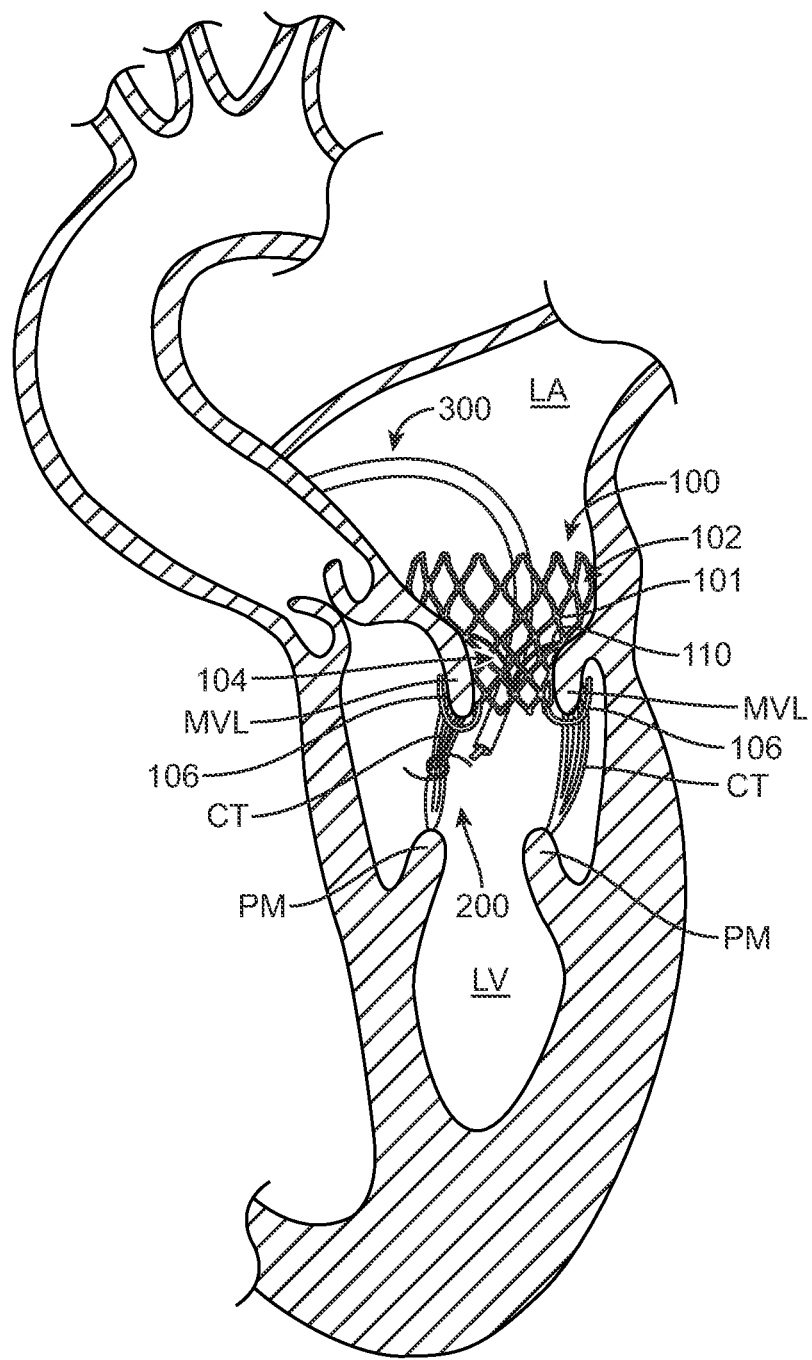

Once the desired rotation of clip 200 is complete, the clip 200 is released from the delivery device 302, as shown in FIG. 12 and step 508 of FIG. 14. For example, and as shown described in the '026 publication, the locking device 352 is operated to release the tether 314. The tether 314 is then removed from engagement (e.g., un-wrapped) with the clip 200, for example by pulling one of the tether sections 346a or 346b proximally from the handle 350. Once the tether 314 is released from the clip 200, the delivery device 302 can be retracted away from the clip 200, as shown in step 510 of FIG. 14.

Figure 13:
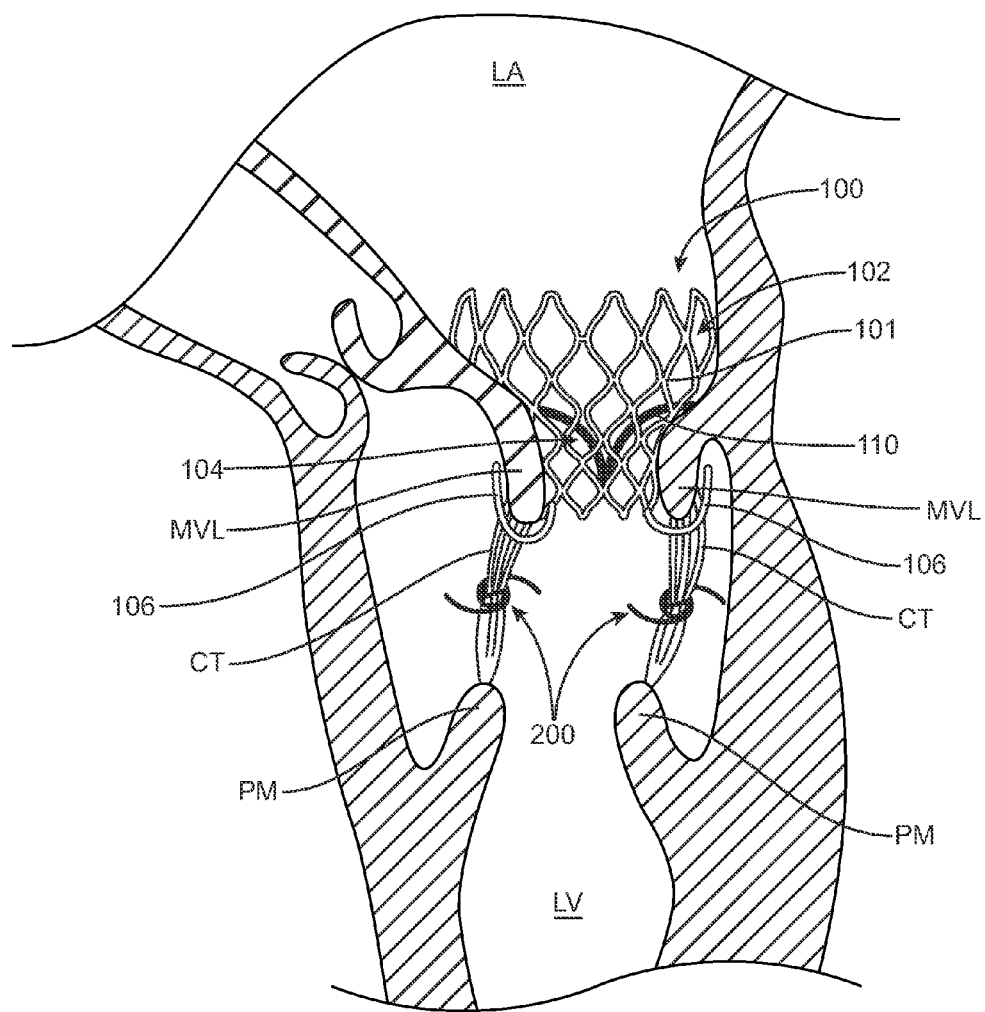

Once delivery device 302 has been retracted, clip 200 remains gathering the chordae tendinae of a mitral valve leaflet, as shown in FIG. 13. FIG. 13 shows two clips 200, one gathering the chordae tendinae of one of the mitral valve leaflets and the second gathering the chordae tendinae of the second valve leaflet. It is understood that the method described in with respect to FIGS. 8-12 and 14 is for delivering and deploying one of the clips 200 to gather/capture the chordae tendinae of one of the mitral valve leaflets MVL (on the left as shown in FIGS. 8-12). However, the method may be repeated to deliver and deploy another clip 200 to gather/capture the chordae tendinae of the other mitral valve leaflet MVL. Further, although not shown, it would be understood by those skilled in the art that additional clips 200 may be delivery and deployed to the chordae tendinae of each of the mitral valve leaflets MVL. For example, and not by way of limitation, one, two, or three clips 200 may be delivered and deployed to gather/capture the chordae tendinae of one of the mitral valve leaflets MVL and zero, one, two, or three clips 200 may be delivered and deployed to gather/capture the chordae tendinae CT of the other mitral valve leaflet MVL.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. For example, different clips may be utilized. Further, different stented valve prostheses may be utilized. Accordingly, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method for treating paravalvular leakage at a location of a prosthetic valve comprising the steps of:
   delivering a clip to a location adjacent chordae tendinae of a native valve; and
   deploying the clip such that the clip captures at least some of the chordae tendinae of the native valve, thereby increasing tension in the captured chordae tendinae.

2. The method of claim 1, wherein the step of deploying the clip comprises releasing the clip from a sheath such that the clip converts from a collapsed state to an undeflected state.

3. The method of claim 2, wherein the step of releasing the clip from the sheath comprises retracting the sheath relative to the clip.

4. The method of claim 2, wherein the step of deploying the clip further comprises rotating the clip in the undeflected state adjacent the chordate such that the clip captures at least some of the chordae tendinae as the clip is being rotated.

5. The method of claim 4, wherein the step of deploying the clip further comprises releasing the clip from a delivery device.

6. The method of claim 1, wherein the prosthetic valve comprises:
   a stent frame;
   support arms extending from a distal portion of the stent frame and bent backwards such that leaflets of the native valve are disposed between the support arms and an outer surface of the stent frame; and
   a prosthetic valve component.

7. The method of claim 1, wherein the native valve is the mitral valve.

8. The method of claim 1, further comprising the steps of;
   delivering a second clip to a location adjacent the chordae tendinae of the native valve; and
   deploying the second clip such that the second clip captures at least some of the chordate tendinae of the native valve, thereby increasing tension in the capture chordae tendinae.

9. The method of claim 8, wherein the clip captures the chordae tendinae coupled to one leaflet of the native valve and wherein the second clip captures the chordae tendinae coupled to a different leaflet of the native valve.

10. The method of claim 8, wherein both the clip and the second clip capture the chordae tendinae coupled to the same leaflet of the native valve.

11. The method of claim 1, further comprising the step of detecting paravalvular leakage around the prosthetic valve prior to the steps of delivering and deploying the clip.

12. A method of implanting a prosthetic valve and treating paravalvular leakage comprising the steps of:
    tracking a prosthetic valve delivery system to the native mitral valve in a radially compressed configuration for delivery;
    deploying the prosthetic valve at the native mitral valve;
    detecting paravalvular leakage at the prosthetic valve implantation site;
    delivering a clip to a location adjacent chordae tendinae of the native mitral valve; and
    deploying the clip such that the clip captures at least some of the chordae tendinae of the native mitral valve, thereby increasing tension in the captured chordae tendinae.

13. The method of claim 12, wherein the prosthetic valve delivery system includes a valve prosthesis having a tubular stent, a prosthetic valve component disposed within and secured to the stent, and at least two support arms coupled to and distally extending from a distal end of the stent when the stent is in the radially compressed configuration.

14. The method of claim 13, wherein the step of deploying the prosthetic valve comprises:
    retracting an outer sheath of the prosthetic valve delivery system to expose the support arms, wherein each support arm bends radially outward and then towards an outer surface of the stent; and
    further retracting the outer sheath to expose the stent, thereby allowing the stent to self-expand into the deployed configuration.

15. The method of claim 12, wherein the step of detecting paravalvular leakage is selected from the methods consisting of intravascular ultrasound, transesophageal echocardiography, and intracardiac echocardiography.

16. The method of claim 12, wherein the step of deploying the clip comprises releasing the clip from a sheath such that the clip converts from a collapsed state to an undeflected state.

17. The method of claim 16, wherein the step of releasing the clip from the sheath comprises retracting the sheath relative to the clip.

18. The method of claim 16, wherein the step of deploying the clip further comprises rotating the clip in the undeflected state adjacent the chordate such that the clip captures at least some of the chordae tendinae as the clip is being rotated.

19. The method of claim 18, wherein the step of deploying the clip further comprises releasing the clip from a delivery device.

20. The method of claim 12, further comprising the steps of;
    delivering a second clip to a location adjacent the chordae tendinae of the native valve; and
    deploying the second clip such that the second clip captures at least some of the chordate tendinae of the native valve, thereby increasing tension in the capture chordae tendinae.

21. The method of claim 20, wherein the clip captures the chordae tendinae coupled to one leaflet of the native valve and wherein the second clip captures the chordae tendinae coupled to a different leaflet of the native valve.

22. The method of claim 20, wherein both the clip and the second clip capture the chordae tendinae coupled to the same leaflet of the native valve.

* * * * *